United States Patent
Zhao et al.

(10) Patent No.: US 6,514,602 B1
(45) Date of Patent: Feb. 4, 2003

(54) WATER-FLUSHABLE AND BIODEGRADABLE FILM USEFUL AS BACKSHEETS FOR DISPOSABLE ABSORBENT ARTICLES

(75) Inventors: Jianqun Zhao, Cincinnati, OH (US); Saeed Fereshtehkhou, Cincinnati, OH (US); Gary Wayne Gilbertson, Middletown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/520,676

(22) Filed: Mar. 7, 2000

(51) Int. Cl.$^7$ .............. B32B 3/00; B32B 5/16; B32B 7/02; A61F 13/20
(52) U.S. Cl. .......... 428/212; 428/323; 428/326; 604/358; 604/385.01; 604/385.23
(58) Field of Search ............... 428/323, 212, 428/326; 604/358, 385.01, 385.23

(56) References Cited

U.S. PATENT DOCUMENTS

| | | | |
|---|---|---|---|
| 3,078,849 A | 2/1963 | Morse | 128/290 |
| 3,407,814 A | 10/1968 | George et al. | 128/290 |
| 3,510,587 A | 5/1970 | Marder et al. | 128/284 |
| 3,542,028 A | 11/1970 | Beebe et al. | 128/290 |
| 3,561,447 A | 2/1971 | Alexander | 128/290 |
| 3,665,923 A | 5/1972 | Champaigne, Jr. | 128/290 |
| 3,683,919 A | 8/1972 | Ells | 128/290 |
| 3,913,579 A | 10/1975 | Srinivasan et al. | 128/290 |
| 3,950,578 A | 4/1976 | Laumann | 427/378 |
| 4,830,187 A | 5/1989 | Keyes et al. | 206/524.7 |
| 5,026,363 A | 6/1991 | Pratt | 604/385.1 |
| 5,097,004 A * | 3/1992 | Gallagher et al. | 528/272 |
| 5,190,533 A | 3/1993 | Blackburn | 604/367 |
| 5,207,662 A | 5/1993 | James | 604/385.2 |
| 5,217,803 A * | 6/1993 | McBride et al. | 428/323 |
| 5,254,607 A * | 10/1993 | McBride et al. | 524/52 |
| 5,300,358 A | 4/1994 | Evers | 428/286 |
| 5,384,189 A | 1/1995 | Kuroda et al. | 428/288 |
| 5,417,679 A * | 5/1995 | Toms et al. | 604/370 |
| 5,573,523 A | 11/1996 | Whalen et al. | 604/374 |
| 5,722,966 A | 3/1998 | Christon et al. | 604/364 |
| 5,888,265 A | 3/1999 | Bonaquist et al. | 65/157 |

FOREIGN PATENT DOCUMENTS

| | | |
|---|---|---|
| WO | WO 90/03156 | 5/1990 |
| WO | WO 92/02199 | 2/1992 |
| WO | WO 93/09740 | 5/1993 |
| WO | WO 95/03361 | 2/1995 |
| WO | WO 95/16474 | 6/1995 |
| WO | WO 96/20831 | 7/1996 |

* cited by examiner

*Primary Examiner*—Cynthia H. Kelly
*Assistant Examiner*—L. Ferguson
(74) *Attorney, Agent, or Firm*—Caroline Wei-Berk; Edward J. Milbrada; Ken K. Patel (57) ABSTRACT

A film which is water-flushable and biodegradable that is particularly useful as a backsheet for disposable absorbent articles, and in particular flushable interlabial catamenial products. The film comprises: (1) a relatively thin water-impervious biodegradable layer to maintain the integrity of the film during use and to minimize or prevent aqueous liquids from penetrating through the film; (2) a relatively thick substantially water-soluble layer adjacent the water-impervious layer to cause the film to lose integrity after the film is flushed; and (3) a relatively thin substantially water-permeable layer adjacent the water-soluble layer to control the rate at which water and other aqueous liquids contact, dissolve and disintegrate the water-soluble layer.

13 Claims, 2 Drawing Sheets

WATER-FLUSHABLE AND BIODEGRADABLE FILM USEFUL AS BACKSHEETS FOR DISPOSABLE ABSORBENT ARTICLES

TECHNICAL FIELD

The present application relates to water-flushable and biodegradable films that are useful as backsheets for disposable absorbent articles, especially as backsheets for certain catamenial products.

BACKGROUND OF THE INVENTION

Disposable absorbent articles currently find widespread use in many different applications, including diapers and training pants for infants and children, feminine care products such as sanitary napkins or tampons, adult incontinence products, and health care products such as surgical drapes or wound dressings. The typical disposable absorbent article usually comprises a topsheet, a backsheet and an absorbent core positioned between the backsheet and the topsheet. These products can also include a fastening system for fitting the product onto the wearer.

Depending on the type of use involved, disposable absorbent articles can be subjected to one or more insults from aqueous liquids such as water, urine, menses or blood. As a result, the backsheet materials of these disposable products are typically made of liquid impermeable materials, such as polypropylene or polyethylene films, that exhibit sufficient strength and handling capability so that the disposable absorbent article retains its integrity during use by the wearer and does not allow leakage of the liquid from the product.

Many disposable absorbent articles can be difficult to dispose of into an aqueous environment. For example, attempts to flush many disposable absorbent articles down the toilet can cause blockage of the toilet or pipes connecting the toilet to the sewage system. In particular, the backsheet materials typically used in these disposable absorbent articles generally do not dissolve, disintegrate or disperse readily when flushed down a toilet so that the disposable absorbent article cannot be disposed of in this manner. If the backsheet materials are made very thin in order to reduce the overall bulk of the disposable absorbent article so as to reduce the likelihood of blockage of the toilet or sewage pipe, the backsheet material will typically not exhibit sufficient strength to prevent tearing or ripping as the outer cover material is subjected to the stresses of normal use by the wearer.

In a number of instances, it would be desirable to be able to flush these disposable absorbent articles down the toilet. These include certain catamenial products known as labial or interlabial sanitary napkins or pads that have a portion which at least partially resides within the wearer's vestibule and a portion which at least partially resides external to the wearer's vestibule. Interlabial pads have the potential to provide greater freedom from inconvenience because of their small size and reduced risk of leakage. Indeed, these interlabial pads are small enough to be easily flushed down the toilet, typically without clogging it or the sewage pipes it leads to. However, even though flushable, such products could put a significant environmental demand on sewage treatment or septic tank systems if they are not readily susceptible to degradation and disintegration after being flushed.

To solve this problem, PCT application 96/20831 (Larson), published Jul. 11, 1996, discloses a film that is alleged to be substantially dispersed when contacted with an excess amount of water and can be used as a backsheet in a disposable absorbent article to increase its flushability in a liquid sewage system. This film comprises a water-dispersible layer and a barrier layer. The water-dispersible layer comprises a water-dispersible polymer such as polyethylene oxide or polyvinyl alcohol and optionally a non-water dispersible polymer to improve the strength and handling properties of this layer. The barrier layer is typically prepared from a polymer that forms a film that is liquid impermeable such as acrylic acid copolymers, and biodegradable polymers polylactic acid, polycaprolactone and polyhydroxybutyrate/hydroxyvalerate, and optionally a water-dispersible polymer in order to improve the decomposition properties of the barrier layer.

It has been found that the polymers used in these respective water-dispersible and barrier layers need to be carefully selected and formulated to provide the desired mechanical properties for such films, as well as to allow these films to be made by conventional film forming techniques, such as coextrusion. Some desirable mechanical properties for such films include sufficient tensile modulus, strength and extensibility to allow the film to be stretched and elongated without tearing or ripping, as well as sufficient softness and flexibility so that disposable products made from the film are comfortable for the wearer and do not create excessive noise during use. There is also the potential for undesired mold growth to occur if biodegradable polymers are present in film, especially if the film is exposed to high humidity and heat. Also, due to the inherent properties of water-dispersible polymers such as relatively low molecular weight (Mw), they can impart poor mechanical properties to the resultant film and undesirable stickiness when wet.

A potential problem with these films comprising both water-dispersible and barrier layers is the ability to control the degradation and disintegration rate of the film, especially when in use. In disposable absorbent articles where such films are used as backsheets, the water-dispersible layer is most likely to be exposed to aqueous liquid insults during use by the wearer. As a result, the film comprising such a layer could lose integrity over time before it is disposed of and thus potentially lead to a problem such as ripping or tearing of the film that could cause leakage.

Accordingly, it would be desirable to be able to provide a flushable and biodegradable film that could be useful as a backsheet for disposable absorbent articles, especially flushable products such as interlabial catamenial products, has desirable mechanical properties including the ability to be stretched and elongated without tearing or ripping, sufficient softness and flexibility to provide comfort for the wearer without excessive noise generation during use, does not promote undesired mold growth or cause undesired stickiness when wet during use, can be made with conventional film-forming techniques, such as coextrusion, and has controlled rates of degradation and disintegration in the presence of aqueous environments so that the film maintains sufficient integrity during use.

DISCLOSURE OF THE INVENTION

The present invention relates to films which are water-flushable and biodegradable. These films comprise:
 a. a substantially biodegradable layer, which comprises:
  (1) from about 65 to 100% of a substantially water-insoluble biodegradable thermoplastic polymer;
  (2) from 0 to about 35% of a substantially water-soluble thermoplastic polymer;

b. a substantially water-soluble layer adjacent the biodegradable layer, which comprises:
   (1) from about 60 to 100% of a substantially water-soluble thermoplastic polymer;
   (2) from 0 to about 40% of a substantially water-insoluble biodegradable thermoplastic polymer;
c. optionally, but preferably, a substantially water-permeable layer adjacent the water soluble layer, which comprises:
   (1) from about 30 to about 70% of a substantially water-soluble thermoplastic polymer;
   (2) from about 30 to about 70% of a substantially water-insoluble biodegradable thermoplastic polymer;
d. wherein the amount of water-soluble thermoplastic polymer in the water-soluble layer is greater than the amount of water-soluble thermoplastic polymer in the water-permeable layer;
e. wherein the water-soluble layer is substantially thicker than each of the biodegradable and water-permeable layers.

The films of the present invention have extremely desirable mechanical properties including the ability to be stretched and elongated without tearing or ripping, and sufficient softness and flexibility to provide comfort for the wearer without excessive noise generation during use. The films of the present are also breathable with typically relatively high Moisture Vapor Transmission Rates (MVTR). Although the films of the present invention contain biodegradable polymers, they do not promote mold growth, even in the presence of humid and hot environments. Films of the present invention can also be made with conventional film forming techniques, including coextrusion, laminating and coating.

The films of the present invention are particularly useful as backsheets for disposable absorbent articles, and in particular for flushable interlabial pads. Even when wet, the films of the present invention typically do not cause undesired stickiness during use of the absorbent article. The optional water-permeable layer is particularly preferred for films of the present invention used as backsheets. This water-permeable layer controls the rate of disintegration and degradation of the film in the presence of aqueous environments during use so that the film maintains sufficient integrity, yet allows the film to be readily disintegrated after it is flushed.

DETAILED DESCRIPTION OF THE INVENTION

A. Definitions

As used herein, "water-flushable" typically means a film, material or product that is capable of being flushed down a standard toilet.

As used herein, "biodegradable" means a polymer, layer, film or material that is capable of being degraded completely or substantially completely into carbon dioxide, water, biomass and inorganic materials by or in the presence of microorganisms. The biodegradation potential can be estimated by measuring carbon dioxide evolution and dissolved organic carbon removal from a medium containing the substance being tested as the sole carbon and energy source and a dilute bacterial inoculum obtained from the supernatant of homogenized activated sludge. See Larson, "Estimation of Biodegradation Potential of Xenobiotic Organic Chemicals," *Applied and Environmental Microbiology*, Volume 38 (1979), pages 1153–61, which describes a suitable method for estimating biodegradability.

As used herein, "substantially water-soluble" means a polymer, layer, film or material that is capable of being completely or substantially completely solubilized, dissolved or dispersed when in contact with an aqueous environment, in particular water.

As used herein, "substantially water-impervious" means a layer, film or material that is completely or substantially completely impermeable to the passage of aqueous liquids, such as water, therethrough.

As used herein, "substantially water-permeable" means a layer that is capable of permitting or allowing the partial or complete passage of aqueous liquids, such as water, therethrough.

As used herein, "thermoplastic" means a polymer that softens when exposed to heat and returns to its original conditions when cooled to room temperature.

As used herein, the term "comprising" means the various components such as the films, layers, polymers, and materials, used in the present invention can be employed in various combinations and with other optional components, and that the various step used in the present invention can be used in various orders or combinations, so long as the objectives of the present invention are achieved. Accordingly, the term "comprising" encompasses the more restrictive terms "consisting essentially of" and "consisting of."

All amounts, parts, ratios and percentages used herein are by weight unless otherwise specified.

B. Water-Soluble Thermoplastic Polymers

A variety of water-soluble thermoplastic polymers can be used in the present invention. However, preferred water-soluble polymers for use in the present invention will have properties such that they can be more easily processed into films by the use of conventional film forming techniques. Although not required, water-soluble polymers for use in present invention are also preferably biodegradable. Blends of different water-soluble polymers can also be used in the present invention so long as such blends do not significantly adversely affect the desired mechanical properties of the resulting film. Typically, a single type of water-soluble polymer is used in the present invention to avoid compatibility problems.

Water-soluble polymers useful in the present invention include hydroxypropyl cellulose, polyethylene oxide, polypropylene oxide, polyvinyl alcohol and polyvinyl alcohol copolymers, polyvinylpyrollidone, polyvinyl pyridine, gelatinized starch, and interpenetrated networks of starch with ethylene/vinyl alcohol copolymers disclosed in U.S. Pat. No. 5,391,423 (Wnuk et al), issued Feb. 21, 1995 (herein incorporated by reference), nylon copolymers, acrylic acid copolymers, polyethylene glycol, as well as compatible mixtures and blends of these polymers. Particularly preferred water-soluble polymers for use in the present invention include polyethylene oxide available from Union Carbide under the Polyox N-80 designation (Mw 200,000) and polyvinyl alcohol available from Air Products under the Vinex 2034, 2025 and 5030 designations.

C. Water-Insoluble Biodegradable Thermoplastic Polymers

A variety of water-insoluble biodegradable thermoplastic polymers can be used in the present invention. However, preferred water-insoluble biodegradable polymers for use in the present invention will have properties such that they can be more easily processed into films by the use of conventional film forming techniques. Suitable water-insoluble biodegradable polymers will also not promote mold growth, even in the presence of humid and hot environments. Although not required, preferred water-insoluble biodegradable polymers for use in the present invention will be not only aerobically biodegradable but also anaerobically biodegradable.

Blends of different water-insoluble biodegradable polymers can also be used the present invention so long as such blends do not significantly adversely affect the desired mechanical properties of the resulting film. Typically, a single type of water-insoluble biodegradable polymer is used in the present invention to avoid compatibility problems. Preferred water-insoluble biodegradable polymers for use in the present invention will have desirable mechanical properties including the ability to be stretched and elongated without tearing or ripping, and will impart sufficient softness and flexibility to the film to provide comfort without excessive noise generation. Biodegradable polymers with these preferred mechanical properties will have relatively low glass transition temperatures ($T_g$) of about 20° C. or less, preferably about 0° C. or less, most preferably about −5° C. or less. Biodegradable polymers with these preferred mechanical properties will also have a relatively low volume percent of crystallinity ($\Phi_C$), as measure by x-ray diffraction, of from about 2 to about 65%, preferably from about 5 to about 50%, most preferably from about 20 to about 40%. See U.S. Pat. No. 5,489,470 (Noda), issued Feb. 6, 1996 (herein incorporated by reference) which describes x-ray diffraction methods for measuring volume percent crystallinity according to the present invention.

Water-insoluble biodegradable polymers useful in the present invention include poly(lactic acid) polymers; polycaprolactones disclosed in U.S. Pat. No. 5,391,423 (Wnuk et al), issued Feb. 21, 1995 (herein incorporated by reference); aliphatic polyalkylene succinate polymers, polyalkylene succinate adipate copolymers or mixtures thereof disclosed in U.S. Pat. No. 5,849,401 (El-Afandi et al), issued Dec. 15, 1998 and U.S. Pat. No. 5,910,545 (Tsai et al), issued Jun. 8, 1999 (herein incorporated by reference); polyhyroxyalkanoate polymers and copolymers including polyhydroxybutyrate polymers and polyhydroxybutyrate/valerate copolymers disclosed in U.S. Pat. No. 5,391,423 (Wnuk et al), issued Feb. 21, 1995 (herein incorporated by reference), and poly(3-hydroxybutyrate-co-3-hydroxhexanoate), poly(3-hydroxybutyrate-co-3-hydroxyoctanoate), poly(3-hydroxybutyrate-co-3-hydroxynonanoate), poly(3-hydroxybutyrate-co-3-hydroxydecanoate), poly(3-hydroxybutyrate-co-3-hydroxydocosanoate), poly(3-hydroxybutyrate-co-3-hydroxyhexadecanoate), poly(3-hydroxyvalerate-co-3-hydroxyoctanoate), poly(3-hydroxybutyrate-co-3-hydroxyvalerate-co-3-hydroxyoctanoate), poly(3-hydroxybutyrate-co-3-hydroxyvalerate-co-3-hydroxydecanoate), and poly(3-hydroxybutyrate-co-3-hydroxyvalerate-co-3-hydroxyoctanoate-co-3-hydroxydecanoate) copolymers disclosed in U.S. Pat. No. 5,489,470 (Noda), issued Feb. 6, 1996 and U.S. Pat. No. 5,498,692 (Noda), issued Mar. 12, 1996 (herein incorporated by reference); aliphatic-aromatic copolyesters preferably comprising 10 to 1000 repeating units, most preferably from 15 to 600 repeating units, disclosed in U.S. Pat. No. 5,292,783 (Buchanan et al), issued Mar. 8, 1994, U.S. Pat. No. 5,446,079 (Buchanan et al), issued Aug. 29, 1995, U.S. Pat. No. 5,559,858 (Buchanan et al), issued Feb. 4, 1997, and U.S. Pat. No. 5,580,911 (Buchanan et al), issued Dec. 3, 1996 (herein incorporated by reference) that are prepared from combinations of dicarboxylic acids or derivatives thereof including those selected from malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, 2,5-norbornanedicarboxylic, 1,4-terephthalic, 1,3-terephthalic, 2,6-naphthoic, and 1,5-naphthoic acid, and ester forming derivatives thereof, and combinations thereof, and diols selected from ethylene glycol, diethylene glycol, propylene glycol, 1,3-propanediol, 2,2-dimethyl- 1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, tetraethylene glycol, and combinations thereof; aliphatic polyesteramides disclosed in U.S. Pat. No. 5,644,020 (Timmermann et al), issued Jul. 1, 1997 (herein incorporated by reference) that are prepared from various combinations of diols such as ethylene glycol, 1,4-butanediol, 1,3-propanediol, 1,6-hexanediol, and diethylene glycol, dicarboxylic acids such as oxalic acid, succinic acid, and adipic acid (or their respective esters), hydroxycarboxylic acids and lactones such as caprolactone, aminoalcohols such as ethanolamine and propanolamine, cyclic lactams such as .epsilon.-caprolactam or lauric lactam, omega-aminocarboxylic acids such as aminocaproic acid, mixtures (1:1 salts) of dicarboxylic acids such as adipic acid and succinic acid and diamines such as hexamethylenediamine and diaminobutane, and hydroxy-terminated or acid-terminated polyesters with molecular weights from about 200 to about 10,000; as well as compatible mixtures or blends of these polymers, such as, for example, poly(tetramethylene succinate-co-terephthalate) copolyesters, poly(tetramethylene glutarate-co-terephthalate) copolyesters, poly(tetramethylene terephthalate-co-diglycolate) copolyesters, poly(tetramethylene glutarate-co-naphthalate) copolyesters and poly(tetramethylene) adipate-co-terephthalate copolyesters.

Particularly preferred water-insoluble biodegradable polymers for use in the present invention that are relatively easy to process into films by conventional techniques and have particularly desirable mechanical properties include poly(lactic acid) polymers; polycaprolactones; aliphatic polyalkylene succinate polymers, polyalkylene succinate adipate copolymers or mixtures thereof; aliphatic-aromatic copolyesters; and polyesteramides. Aliphatic polyalkylene succinate polymers, polyalkylene succinate adipate copolymers or mixtures thereof that are particularly preferred for use in the present invention include polybutylene succinate polymers and polybutylene succinate adipate copolymers having weight-averaged molecular weights (Mw) of from about 40,000 to about 300,000 with a degree of polydispersity (Mw/Mn) in the range of from about 1.8 to about 3.6 and are available from Showa Highpolymer Co. Ltd, Tokyo, Japan, under the Bionolle Type 1000 and 3000 designations. Aliphatic-aromatic copolyesters that are particularly preferred for use in the present invention include poly (tetramethylene) adipate-co-terephthalate copolyesters available from Eastman Chemical under the Eastar Biodegradable Copolyester 14776 designation. Aliphatic polyesteramides that are particularly preferred for use in the present invention include those prepared from combinations of adipic acid, butanediol or hexanediol, and aminocaproic acid or $\epsilon$-caprolactam, having averaged molecular weights (Mw) of from about 50,000 to about 200,000 that are available from Bayer under the BAK 402, 403 and 404 designations.

D. Composition and Characteristics of Film

The key characteristics of the films of the present invention are that they are water-flushable and biodegradable. Other important characteristics of such films are that they have extremely desirable mechanical properties including the ability to be stretched and elongated without tearing or ripping, and sufficient softness and flexibility to provide comfort for the wearer without excessive noise generation during use. The degree to which the films of the present invention can be stretched and elongated is defined by the percent elongation at break in both the machine direction (MD) and the cross machine direction (CD). Basically, the percent elongation at break measures how much the film can be pulled and stretched in a given direction before the film breaks or ruptures. Films of the present invention typically have a percent elongation at break in either the MD or CD direction (preferably in both directions) of at least about 150%, preferably at least about 200% and most preferably at least about 250%, as measured according the test method described in Section G(1) below.

The films of the present invention should also not promote mold growth, even in presence of humid and hot environments. See test method described in Section G(4) below. Indeed, the films of the present invention can be formulated to provide the combined advantages of eliminating mold growth, improving mechanical film properties, and overcoming undesired stickiness when the film is wet. Preferred films of the present invention are also breathable and have relatively high Moisture Vapor Transmission Rates (MVTR), typically at least about 500 g/m$^2$/24 hours, preferably at least about 1000 g/m$^2$/24 hours, as measured according the test method described in Section G(2) below.

Films of the present invention can be prepared to any desired thickness, so long as they remain water-flushable and biodegradable. In the case of backsheets for disposable absorbent articles, such films are relatively thin. Suitable films for such backsheets typically have a thickness of from about 0.5 to about 3 mil (13–76 $\mu$). Preferably, such films have a thickness of from about 0.7 to about 1.6 mil (18–41$\mu$).

The films of the present invention usually comprise the following layers: (1) a substantially biodegradable layer; (2) a substantially water-soluble layer adjacent the biodegradable layer; and (3) optionally but preferably a substantially water-permeable layer adjacent the water-soluble layer. In the films of the present invention, the water-soluble layer is substantially thicker than each of the biodegradable and water-permeable layers. By "substantially thicker" is meant that the water-soluble layer is sufficiently thicker relative to the thickness of each of the biodegradable and water-permeable layers such that the film, after it is flushed, will eventually and preferably rapidly lose integrity as the relatively thick water-soluble layer is dissolved and disintegrated, leaving behind the relatively thin biodegradable and water-permeable layers that take up a significantly smaller volume. Typically, the water-soluble layer is at least about 2 times as thick as each of the biodegradable and water-permeable layers. Preferably, the water-soluble layer is at least about 3 times as thick as the biodegradable and water-permeable layers.

For films of the present invention which do not comprise the optional water-permeable layer, the water-soluble layer typically comprises from about 70 to about 95%, preferably from about 80 to about 90%, of the thickness of the entire film, while the biodegradable layer comprises from about 5 to about 30%, preferably from about 10 to about 20%, of the thickness of the entire film. For films of the present invention which do comprise the optional but preferred water-permeable layer, the water-soluble layer typically comprises from about 50 to about 95%, preferably from about 60 to about 80%, of the thickness of the entire film, while the biodegradable and water permeable layers each comprise from about 2.5 to about 25%, preferably from about 5 to about 20%, of the thickness of the entire film.

The biodegradable layer maintains the integrity of the film during use, but after it is flushed, is degraded and disintegrated by microorganisms in the aqueous environment, in the septic tank or in the sewage treatment facility. See test method described in Section G(3) below. When substantially water-impervious (e.g., when used as a backsheet), this biodegradable layer also minimizes or prevents moisture from penetrating through the film from the outside and minimizes or prevents aqueous liquids from escaping through the film from the inside. See test method described in Section G(5) below. The thickness of this biodegradable layer can vary as desired within the previously defined constraints with regard to the other layers of the film. Typically, this biodegradable layer has a thickness of from about 0.05 to about 0.5 mil. Preferably, this biodegradable layer has a thickness of from about 0.1 to about 0.3 mil.

This biodegradable layer comprises from about 65 to 100% of a substantially water-insoluble biodegradable thermoplastic polymer as previously defined, and from about 0 to about 35% of a substantially water-soluble thermoplastic polymer as previously defined. The particular amounts used will depend on the particular polymers involved, the properties, in particular mechanical properties desired, the intended use of the film and like factors. The inclusion of the minor amount of water-soluble thermoplastic polymer allows this water-impervious layer to lose at least some of its integrity after the film is flushed, yet maintain sufficient integrity during use before flushing. Typically, the biodegradable layer comprises from about 70 to 100% of a water-insoluble biodegradable polymer, and from 0 to about 30% of a water-soluble polymer. Preferably, the biodegradable layer comprises from about 80 to 100% of a water-insoluble biodegradable polymer, and from 0 to about 20% of a water-soluble polymer.

The substantially water-soluble layer adjacent the biodegradable layer causes the film to eventually and preferably rapidly lose integrity after the film is flushed, leaving behind a relatively small volume of any residual water-insoluble material. The thickness of this water-soluble layer can vary as desired within the previously defined constraints with regard to the other layers of the film and is especially dependent on whether the optional but preferred water-permeable layer is present in the film. For films of the present invention which do not comprise the optional water-permeable layer, the water-soluble layer typically has a thickness of from about 0.3 to about 1.5 mil (8–38$\mu$), preferably from about 0.6 to about 1.3 mil (15–33$\mu$). For films of the present invention which do comprise the optional water-permeable layer, the water-soluble layer typically has a thickness of from about 0.5 to about 1.2 mil (13–30$\mu$), preferably from about 0.6 to about 1.0 mil (15–25$\mu$).

This water-soluble layer comprises from about 60 to 100% of a substantially water-soluble thermoplastic polymer as previously defined, and from 0 to about 40% of a substantially water-insoluble biodegradable thermoplastic polymer as previously defined. The particular amounts used will depend on the particular polymers involved, the properties, in particular the rate of degradation and disintegration desired in the presence of an aqueous environment such as water, the intended use of the film and like factors. The inclusion of a minor amount of water-insoluble thermoplastic biodegradable polymer allows this water-soluble layer to have improved mechanical properties and to maintain sufficient integrity during use before flushing, yet allows this layer to dissolve and lose integrity after the film is flushed. Typically, the water-soluble layer comprises from about 60 to about 95% of a water-soluble polymer, and from about 5 to about 40% of a water-insoluble biodegradable polymer. Preferably, the water-soluble layer comprises from about 70 to about 90% of a water-soluble polymer, and from about 10 to about 30% of a water-insoluble biodegradable polymer.

The preferred substantially water-permeable layer controls the rate at which water and other aqueous body liquids contact the adjacent the water-soluble layer. By controlling the rate at which water and other aqueous body liquids contact the adjacent water-soluble layer, this also controls rate at which the water-soluble layer dissolves and disintegrates, and so controls the rate at which the overall film loses integrity, degrades and disintegrates. Initially, contact of the water-permeable layer with low levels of aqueous fluids causes minimal amounts of the water-soluble polymer present therein to be solubilized and dissolved away, allowing minimal amounts of aqueous liquids to pass therethrough. However, as this water-permeable layer comes in contact with increasing amounts of aqueous liquids, especially after the film is flushed, the water-soluble polymer present in this layer is increasingly solubilized and dissolved away. As a result, this layer becomes more and more water-permeable and thus allows aqueous liquids to pass through this layer at an increasing rate into the adjacent water-soluble layer, thus causing the water-soluble layer to be solubilized and dissolved away more rapidly.

For example, in the case of backsheets used in disposable absorbent articles, this water-permeable layer is typically in contact with the absorbent core. While this absorbent core provides an aqueous environment as a result of aqueous liquid insults to the absorbent article, the amount of aqueous liquid generated is usually insufficient to cause more than minimal solubilization of the water-soluble polymer present in the water-permeable layer. However, when absorbent article is flushed, the amount of aqueous liquid present is more than sufficient to cause the water-soluble polymer present in the water-permeable layer to be solubilized and dissolve away. This causes the adjacent water-soluble layer to be increasingly exposed to aqueous liquid that solubilizes and dissolves the water-soluble polymer in this layer, thus causing the water-soluble layer to be rapidly dissolved and disintegrated.

The thickness of this water-permeable layer can vary as desired within the previously defined constraints with regard to the other layers of the film. Typically, this water-permeable layer has a thickness of from about 0.05 to about 0.5 mil (1–13µ). Preferably, this water-permeable layer has a thickness of from about 0.1 to about 0.3 mil (2–8µ).

This water-permeable layer comprises from about 30 to about 70% of a substantially water-soluble thermoplastic polymer as previously defined, and from about 30 to about 70% of a substantially water-insoluble biodegradable thermoplastic polymer as previously defined. The particular amounts used will depend on the particular polymers involved, the properties, in particular the aqueous liquid control properties desired, the intended use of the film and like factors. In order for this layer to control the rate at which aqueous liquids pass through to the adjacent water-soluble layer, the amount of water-soluble thermoplastic polymer in the water-soluble layer needs to be greater than the amount of water-soluble thermoplastic polymer in the water-permeable layer. Preferably, the water-permeable layer comprises from about 40 to about 60% of a water-soluble polymer, and from about 40 to about 60% of a water-insoluble biodegradable polymer.

E. Methods for Making Film

The films of the present invention can be made by conventional film-forming techniques for making multilayer films. (When using blends of biodegradable and water-soluble polymers to form the respective layers of the films, the biodegradable and water-soluble polymers are typically fed together through a twin screw extruder, with the resulting extruded blend being cooled and then pelletized using a conventional pelletizer.) Suitable film-forming methods include coextrusion, lamination, coating, cast film, blown-film and like methods. Coextrusion methods typically require more than one extruder such as a coextrusion feedblock system, a multi-manifold die system or combinations of these systems. See U.S. Pat. No. 5,391,423 (Wnuk et al), issued Feb. 21, 1995 (herein incorporated by reference), for a further description of conventional coextrusion techniques. Processing aids such as antiblocks (e.g., talc) can be desirable in preparing certain of the extruded films of the present invention. See, for example, U.S. Pat. No. 5,292,783, supra, which discloses some representative processing aids for extruded films made with aliphatic-aromatic copolyesters.

U.S. Pat. Nos. 4,152,387, and 4,197,069, disclose the feedblock principle of coextrusion. Multiple extruders are connected to the feedblock which employs moveable flow dividers to proportionally change the geometry of each individual flow channel in direct relation to the volume of polymer passing through said flow channels. The flow channels are designed such that at their point of confluence, the materials flow together at the same flow rate and pressure eliminating interfacial stress and flow instabilities. Once the materials are joined in the feedblock, they flow into a single manifold die as a composite structure. It is important in such processes that the melt viscosities and melt temperatures of the materials do not differ too greatly; otherwise flow instabilities can result in the die leading to poor control of layer thickness distribution in the film.

An alternative to feedblock coextrusion is a multi-manifold or vane die as disclosed in aforementioned U.S. Pat. Nos. 4,152,387 and 4,197,069, and in U.S. Pat. No. 4,533,308. In contrast to the feedblock system where melt streams are brought together outside and prior to entering the die body, a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same linear flow rate, pressure, and desired width.

F. Uses of Film

Because of the unique properties of the water-flushable and biodegradable films of the present invention, they are especially suitable for use in absorbent articles, especially disposable absorbent articles. As used herein, the "absorbent article" refers to articles that absorb and contain aqueous body liquids, and more specifically refers to articles that are placed against or in proximity to the body of the wearer to absorb and contain the various aqueous liquids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article can be recycled, reused, composted or flushed). An embodiment of a disposable absorbent article according to the present invention is a diaper. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, pantiliners, tampon applicators, facial tissues, paper towels, breast pads, and the like, as well as other potentially flushable items, such as tampon applicators, wrappers and packaging for various products, including disposable absorbent articles, disposable gloves and the like.

These absorbent articles typically comprise a substantially water-impervious backsheet made from the film of the present invention, a substantially water-permeable topsheet joined to, or otherwise associated with the backsheet, and an absorbent core positioned between the backsheet and the topsheet. The topsheet is positioned adjacent the body surface of the absorbent core. The topsheet is preferably joined to the absorbent core and to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In preferred absorbent articles, the topsheet and the backsheet are joined directly to each other at the periphery thereof. The topsheet and backsheet can also be indirectly joined together by directly joining them to the absorbent core by the attachment means.

The topsheet is compliant, soft feeling, and non-irritating to the wearer's skin. Further, the topsheet is water-permeable to permit aqueous body liquids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. Preferred topsheets for use in absorbent articles of the present invention are selected from high loft nonwoven topsheets and aperture formed film topsheets. A suitable nonwoven material is known as COROLIND and is available from Corovin, GmbH, Peine, Germany. A preferred version of this topsheet is a nonwoven material such as COROLIND that has been subjected to a process known as SELFing, which process is described in U.S. Pat. No. 5,518,801, issued to Chapell et al. on May 21, 1996 and which is hereby incorporated by reference.

Apertured formed films are especially preferred for the topsheet because they are permeable to aqueous body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents being incorporated herein by reference. Particularly preferred microapertured formed film topsheets are disclosed in U.S. Pat. No. 4,609,518 (Curro et al), issued Sep. 2, 1986 and U.S. Pat. No. 4,629,643 (Curro et al), issued Dec. 16, 1986, which are all incorporated by reference. The preferred topsheet for use in catamenial products of the present invention is the formed film described in one or more of the above patents and marketed on sanitary napkins by The Procter & Gamble Company of Cincinnati, Ohio as "DRI-WEAVE®."

The body surface of the formed film topsheet can be hydrophilic so as to help aqueous body liquids to transfer through the topsheet faster than if the body surface was not hydrophilic so as to diminish the likelihood that liquid will flow off the topsheet rather than flowing into and being absorbed by the absorbent structure. In one embodiment, surfactant can be incorporated into the polymeric materials of the formed film topsheet such as is described in U.S. Statutory Invention Registration H1670, published Jul. 1, 1997 in the name of Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

In an alternative embodiment according to the present invention, the film the present invention can be used to provide a topsheet for such an absorbent article. In this alternative embodiment, the biodegradable layer of the film is adjacent the wearer's body or skin, while the water-permeable layer of the film is adjacent the absorbent core. Nominally, the biodegradable layer of the film is water-impervious such that the film is also water-impervious. However, this biodegradable layer, as well as the film, can be made water-permeable by preparing the film of the present invention as an apertured formed film, as previously described for other apertured formed film topsheets.

The absorbent core of the absorbent article is positioned between the topsheet and backsheet. The absorbent core can be manufactured in a wide variety of sizes and shapes (e.g., rectangular, hour-glass, asymmetrical, etc.) and from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, rayon including needle punched rayon, and thin layers of foam. The absorbent core can comprise a single material. Alternatively, the absorbent core can comprise a combination of materials. The total absorbent capacity of the absorbent core should, however, be compatible with the designed liquid loading for the intended use of the absorbent article. Further, the size and absorbent capacity of the absorbent core can vary to accommodate wearers ranging from infants through adults.

Figure 1:
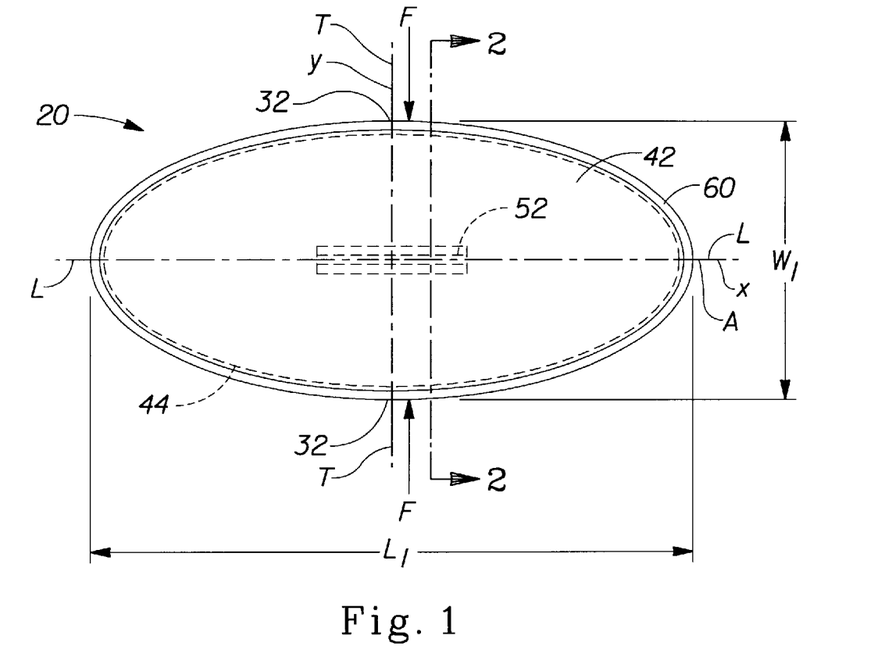
FIG. 1 is a top plan view of an absorbent interlabial pad for which the films the resent invention are useful as backsheets.
Figure 2:
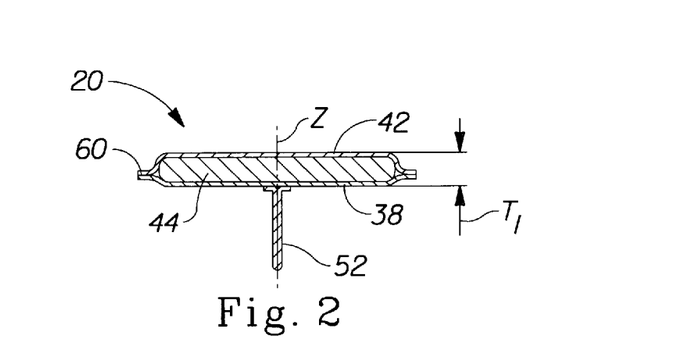
FIG. 2 is a cross sectional view of the absorbent interlabial pad of FIG. 1, taken along line 2—2.
Figure 3:
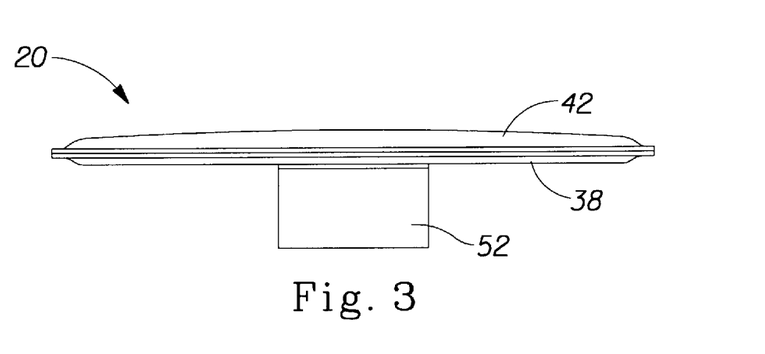
FIG. 3 is a side view of the absorbent interlabial pad of FIG. 1.

The films of the present invention are particularly useful as water-impervious backsheets for interlabial pads such as those shown in FIGS. 1–3. As used herein the term "absorbent interlabial pad" refers to a structure which has at least some absorbent components, and which is specifically configured to reside within the interlabial space of a female wearer during use. When the absorbent interlabial pad 20 is properly sized for an individual wearer, more than half of the entire absorbent interlabial pad 20 resides within such interlabial space. Preferably substantially the entire absorbent interlabial pad 20 resides within such interlabial space, and more preferably the entire absorbent interlabial pad 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minora, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial pad into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial pad 20 shown in FIG. 1 has a longitudinal centerline L which runs along the "x" axis. The term "longitudinal", as used herein, refers to a line, axis or direction in the plane of the interlabial pad 20 that is generally aligned with (e.g., approximately parallel to) a vertical plane which bisects a standing wearer into left and right body halves when the interlabial pad 20 is worn. The terms "transverse," "lateral," or "y direction" as used herein, are interchangeable, and refer to a line axis or direction that is generally perpendicular to the longitudinal direction. The lateral direction is shown in FIG. 1 as the "y" direction. The absorbent interlabial pad 20 shown in FIG. 1 also has a transverse centerline T. The "z" direction, shown in FIG. 2, is a direction parallel to the vertical plane described above. The term "upper" refers to an orientation in the z-direction toward the wearer's head. "Lower" or downwardly is toward the wearer's feet.

As shown in FIGS. 1–2, the interlabial pad comprises at least a water-permeable topsheet 42, a water-impervious backsheet 38 joined to the topsheet 42, and an absorbent core 44 positioned between the topsheet 42 and the backsheet 38. The interlabial pad 20 must be of a suitable size and shape that allows at least the majority of the pad 20 to fit comfortably within the wearer's interlabial space and to cover the wearer's vaginal orifice, and preferably also the wearer's urethra. The interlabial pad 20 at least partially blocks, and more preferably completely blocks and intercepts the flow of menses, urine, and other bodily exudates from the wearer's vaginal orifice and urethra.

The size of the interlabial pad 20 is important to its comfort and effectiveness. The length of the absorbent interlabial pad 20 is measured along the longitudinal centerline L in the longitudinal direction (or "x"-direction). The absorbent interlabial pad 20 preferably has a length $L_1$ which is greater than about 60 mm and less than about 130 mm. More preferably, the length $L_1$ is between about 90 mm and about 105 mm. The width of the interlabial pad 20 is measured along the transverse centerline T in the transverse direction (or "y"-direction). The absorbent interlabial pad 20 preferably has a width $W_1$ which is between about 25 mm and about 50 mm. The thickness (or caliper) is the "z"-direction dimension of the pad 20. Caliper measurements given herein were measured using an AMES gage with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper $T_1$ of the absorbent interlabial pad 20 is less than the width $W_1$ and the length $L_1$ of the pad 20. Preferably the caliper $T_1$ of the absorbent interlabial pad 20 is less than or equal to about 8 mm, more preferably the caliper $T_1$ is less than about 6 mm, and even more preferably less than about 4 mm.

The topsheet 42 comprises a first liquid permeable component. The topsheet 42 should be compliant, soft feeling, and non-irritating to the wearers skin. Further, the topsheet 42 is liquid permeable permitting liquids (e.g., menses and/or urine) to readily penetrate through its thickness. A suitable topsheet 42 may be manufactured from a wide range of materials previously described as suitable for topsheets in other absorbent articles. For example, a suitable topsheet 42 is a nonwoven material formed of rayon fibers with a basis weight of about 18 g/m² and is available from Veratec of Walpole, Mass. sold under the designation grade 9313709070. This material is particularly suitable for use as a topsheet 42 because it is a biodegradable. The topsheet 42 can also comprise an apertured formed film as previously described, preferably a "DRI-WEAVE" topsheet. Alternatively, an apertured formed film prepared according to the present invention with the biodegradable layer adjacent the body of the wearer and the water-permeable layer adjacent the absorbent core can be used.

In a preferred embodiment of the interlabial pad, the body surface of the formed film topsheet is hydrophilic to help liquids transfer through the topsheet 42 faster than if the body surface was not hydrophilic so as to diminish the likelihood that menstrual fluid will flow off the topsheet 42 rather than flowing into and being absorbed by the absorbent core 44. The body surface of the topsheet 42 can be made hydrophilic by treating it with a surfactant or by incorporating the surfactant into the polymeric materials of the formed film topsheet, as previously described.

The inner surface of topsheet 42 may be secured in contacting relation with an underlying absorbent layer. This contacting relationship results in liquid penetrating topsheet 42 faster. The topsheet 42 may be kept in a contacting relationship with an underlying layer by bonding the topsheet 42 to the underlying layer. However, it is not absolutely necessary to bond the face of the topsheet 42 to the face of the underlying layer. The topsheet 42 can be maintained in contact with an underlying absorbent component, by entangling the fibers of the underlying layer with the topsheet, by fusing the topsheet 42 to an underlying absorbent layer by a plurality of discrete individual fusion bonds, or by any means known in the art.

It is not necessary that the topsheet 42 comprise a layer or material which is separate or distinct from the absorbent core 44. The topsheet 42 and absorbent core 44 may consist of one unitary structure in which the body-contacting surface of the absorbent core 44 will serve as the liquid permeable topsheet 42. In such an embodiment, the liquid permeable body contacting surface may be hydrophilic or treated so as to render it hydrophilic such that fluids readily penetrate through the surface and into the interior of the absorbent core 44. Additionally, the unitary topsheet 42 and absorbent core 44 may be provided with a pore size, capillary, or hydrophilicity gradient to assist in the absorption and retention of fluids in the interior of the absorbent core 44.

The absorbent core 44, which is best seen in FIG. 2, is positioned between the topsheet 42 and the backsheet 38. The absorbent core 44 provides the means for absorbing exudates such as menses and other aqueous body liquids. The absorbent core 44 preferably is generally compressible, conformable, and non-irritating to the user's skin. The absorbent core 44 can comprise any suitable material that is capable of absorbing and/or retaining liquids (e.g. menses and/or urine), as previously described for other absorbent articles. A particularly preferred material for the absorbent core 44 is batt of rayon or a rayon/cotton blend. A tri-lobed rayon known as GALAXY rayon available from Courtaulds Fibers, Inc. of Axis, Ala. has been found to work well for the material comprising the absorbent core 44.

Preferably, the absorbent core 44 has the same general shape as the overall absorbent interlabial pad 20. The absorbent core 44 (and the overall absorbent interlabial pad 20) may be manufactured in a wide variety of shapes. Non limiting examples of 20 shapes for the absorbent core 44 when viewed from the top as in FIG. 1 include ovoid, elliptical, trapezoidal, rectangular, triangular, diamond-shaped or any combination of the above. As shown in FIG. 1, the preferred shape for the absorbent core 22 and the overall absorbent interlabial pad 20 is generally ovoid or elliptical.

The backsheet 38, which is best shown in FIGS. 2 and 3, is made from films according to the present invention where the biodegradable layer is a water-impervious outer layer and where the water-permeable layer is adjacent the absorbent core 44. Backsheet 38 prevents the exudates absorbed and contained in the absorbent core 44 from wetting articles and/or body parts which may contact the absorbent interlabial pad 20 such as pants, pajamas, undergarments, pubic hair, the wearer's thighs, etc. The backsheet 38 should be flexible and impervious to liquids (e.g., menses and/or urine). As used herein, the term "flexible" refers to materials which are compliant and will readily conform to the general shape and contours of the human body. The backsheet 38 also provides protection for the wearer's fingers as the absorbent interlabial pad 20 is inserted, or as the pad is optionally removed with the fingers.

The components of the absorbent interlabial pad 20 described above (topsheet 42, backsheet 38, absorbent core 44) can be assembled in any suitable manner. In the preferred embodiment shown in FIGS. 1–3, the components of the main body portion are assembled in a "sandwich" configuration with the components sized so that the edges of the topsheet 42 and backsheet 38 extend outward beyond the edges of the absorbent core 44. The topsheet 42 and backsheet 38 are preferably at least partially peripherally joined using known techniques. As shown in FIGS. 1 and 2, the topsheet 42 is preferably secured to backsheet 38 along a seam, such as seam 60. Seam 60 is preferably liquid impervious. The seam 60 can be formed by any means commonly used in the art for this purpose such as by gluing, crimping, or heat-sealing. The seam 60 and the area of the interlabial pad 20 in the vicinity of the seam 60 should be soft, compressible, and conformable. If the seam 60 and surrounding area are too stiff or non-compressible, the wearer may experience discomfort when wearing the interlabial pad 20.

The components of the absorbent interlabial pad 20 can be joined together by adhesives, stitching, heat and/or pressure bonds, dynamic mechanical bonds, ultrasonic bonds, intermingling or entanglement of the fibers or other structural elements comprising the components of the absorbent interlabial pad 20, such as by meltblowing the fibers comprising one component onto another component, extruding one component onto another, or by any other means known in the art. The components of the absorbent interlabial pad 20 may be joined with water soluble adhesives in order to increase the tendency of the pad 20 to disperse into a plurality of fragments in mildly agitated water (such as in a toilet).

The absorbent interlabial pad 20 in its fully assembled configuration comprises at least one axis of preferred bending A. The axis of preferred bending A is preferably located generally along the longitudinal centerline L of the absorbent interlabial pad 20. The axis of preferred bending A is a line or axis along which the absorbent interlabial pad 20 will tend to bend or fold when subjected to compressive forces F directed inwardly in the transverse direction at the sides 32 of the pad 20. The axis of preferred bending A may result naturally from the product configuration, or the pad 20 may be imparted with a weakened axis or region in any or all of the topsheet 42, backsheet 38 and core 44 to create the axis of preferred bending A. Such a weakened axis may be created by any variety of known techniques such as scoring, pre-folding, slitting, or the like. The absorbent interlabial pad 20 may comprise a region of preferred bending made up of a plurality of axes of preferred bending. Any number of such axes may comprise such a region of preferred bending up to an infinite number.

Figure 4:
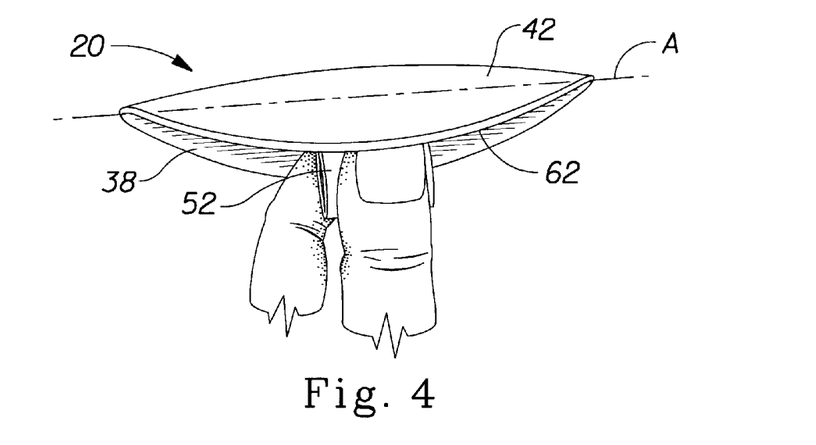
FIG. 4 shows the absorbent interlabial pad of FIG. 1 folded along the axis of preferred bending and being grasped for insertion by the wearer's fingers.

The absorbent interlabial pad 20 is folded along the axis of preferred bending A, as shown in FIG. 4, prior to insertion within the wearer's interlabial space. Once inserted, the pad 20 will preferably tend to unfold slightly keeping the topsheet 42 of the pad 20 in contact with the inner walls of the wearer's labia. The pad 20 may be resiliently biased slightly along the axis of preferred bending A to increase the tendency of the pad 20 to unfold. This allows the folded pad 20 to act as a "spring" under both wet and dry conditions and, consequently, to increase the tendency of the topsheet 42 of the pad to remain in contact with the inner surfaces of the labia when the absorbent interlabial pad 20 is in place. A pad 20 constructed according to the preferred embodiment described above, however, does not necessarily require any additional structural features to provide the ability to maintain such contact. The naturally moist surfaces of the labia will have a tendency to adhere to the material comprising the topsheet 42 further tending to keep the pad 20 in contact with the inner surfaces of the labia.

The interlabial pad 20 may be provided with a permanent crease (not shown) along at least a portion of the axis of preferred bending A. This permanent crease may preferably be created by the process of attaching a removal tab 52 (described in greater detail, below) to the backsheet 38. Such a permanent crease, while still allowing for the topsheet 42 to maintain contact with the inner surfaces of the labia, may assist users in product placement and allow for more intimate contact of the pad with the wearer's interlabial space.

The absorbent interlabial pad 20 described herein is both flexible and compressible. Flexibility and compressibility are important to product comfort. If the absorbent interlabial pad 20 is too flexible, the pad is not conveniently or easily placed between the folds of the labia, if it is too stiff, the pad is uncomfortable and when the user is in a sitting position, the product can be forced forward against the clitoris causing discomfort.

The preferred shape of the absorbent interlabial pad 20 shown in FIGS. 1–3 (i.e., one in which the pad is tapered at the ends) allows the pad to easily and comfortably fit the wearer's interlabial space. A pad 20 with such a tapered shape, when folded along an axis of preferred bending A (as in FIG. 4) will have a profile in which highest point along the axis of bending A (as measured in the "z"-direction) is in the vicinity of the center of the pad 20 rather than at the ends.

The absorbent interlabial pad 20 is preferably provided with an optional removal tab 52 joined to the backsheet 38. The tab 52 may be made of a variety of materials and need not be absorbent. The tab 52 may be formed from a nonwoven material which is heat bonded to a tissue layer. A suitable nonwoven material is known as COROLIND and is available from Corovin, GmbH, Peine, Germany. A suitable airlaid tissue is available from Merfin Hygenic Products, Ltd., of Delta, British Columbia, Canada, having a basis weight of about 61 g/m² and having the designation grade number 176.

The tab 52 may be of any suitable size which provides for a convenient finger grip during insertion and, optionally, removal of the pad 20. In the preferred embodiment shown in FIGS. 1–3, the tab 52 is about 20 mm long, and about 13 mm in height (i.e. measured in the "z"-direction after attachment).

The tab 52 is preferably joined to the surface of the backsheet 38 which faces away from the topsheet 42. The tab 52 provides a location for the wearer to grasp the pad 20 during insertion. The absorbent interlabial pad 20 is designed to be expelled by urination. The tab 52, however, may provide an alternative mechanism for removal of the pad 20 (i.e., removal with the fingers).

As previously discussed, the absorbent interlabial pad 20 is designed to be placed within the interlabial space of a wearer. To use the absorbent interlabial pad 20 of the present invention, the wearer grasps the tab 52 of the pad 20. If the pad 20 is not provided with a tab 52, the wearer may hold the folded pad 20 at the sides 32 and begin insertion. The pad 20 is then further inserted by pushing with a finger or fingers in the recess 62 formed by the folded backsheet 38.

Figure 5:
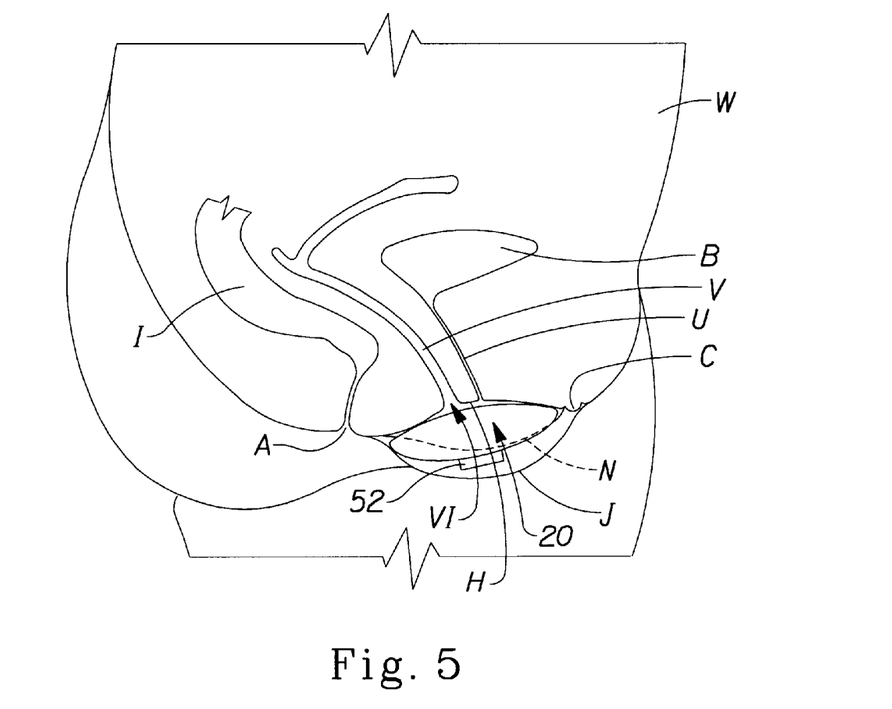
FIG. 5 is a cross-sectional saggital view of a human female wearer showing the placement of the absorbent interlabial pad of FIG. 1 in the wearer's interlabial space.

As shown in FIG. 4, the folded pad 20 forms a recess 62 within the folded backsheet 38 which covers the tips of the wearer's fingers during insertion. This feature provides for a hygienic insertion of the absorbent interlabial pad 20 of the present invention. The wearer may assume a squatting position during insertion to assist in spreading the labial surfaces. FIG. 5 shows a preferred embodiment of the absorbent interlabial pad 20 inserted into the interlabial space of a wearer W. The urogenital members shown in FIG. 5 include the bladder B, the vagina V, the urethra U, the clitoris C, the large intestine I, the anus A, the vaginal introitus VI, the hymeneal ring H, the labia minora N, and the labia majora J. FIG. 5 shows the relationship of these anatomical features of the wearer W to the absorbent interlabial pad 20 when the pad is properly inserted for use. Once the absorbent interlabial pad 20 is inserted, the topsheet 42 tends to adhere to the inside surfaces of the labia. When the wearer is standing, the labial walls close more tightly around the folded absorbent interlabial pad 20.

The interlabial pad 20 is preferably at least partially retained in place by exerting a slight laterally outwardly-oriented pressure on the inner surfaces of the wearer's labia minora, labia majora, or both. Additionally, the product may also be held by attraction of naturally moist labial surfaces to the material comprising the topsheet 42. Optionally, the topsheet 42 of the pad 20 may be provided with a biocompatible adhesive to assist the adhesion of the pad 20 to the inside surfaces of the wearer's labia. The strength of such an adhesive should be selected to assist the absorbent interlabial pad 20 in staying in place, while still allowing for reliable, and comfortable removal of the pad from the wearer's interlabial space.

G. Test Methods

1. Percent Elongation at Break

Percent elongation at break for the films of the present invention are determined according to "Standard Test Method for Tensile Properties of Thin Plastic Sheeting," ASTM Designation D 882–95a (1995), pages 159–167. The percent elongation at break is calculated as shown in paragraph 11.4 of this method.

2. Moisture Vapor Transmission Rate

The Moisture Vapor Transmission Rate (MVTR) for the films of the present invention is determined as follows: A known amount of anhydrous calcium chloride (about 15 grams) is placed in a "cup-like" container. A film sample of known area (approximately 1.25×1.25 inches) is placed on top of the container and held securely thereon by a retaining ring and gasket. This assembly is placed in a chamber having a temperature of 40° C. and a relative humidity of 75% for 5 hours. The amount of moisture absorbed by the calcium chloride during this 5-hour period is determined gravimetrically and then converted to an MVTR value of grams of water per 24 hours per m². Final MVTR values are based on the average of three film samples.

3. Percent Weight Loss During Anaerobic Disintegration

The anaerobic disintegration in terms of percent weight (wt.) loss for the films of the present invention is determined as follows: The sludge used in this method is an anaerobic sludge obtained from a municipal waste water treatment plant/digester. The sludge is sieved (1 mm. screen), has a pH of about 7–8 with at least about 1% total solids. The film sample to be evaluated of known weight is added to a flask containing 1200 ml. of the sludge and the flask is then covered with a one-hole rubber stopper to allow for the venting of evolved gases and is placed in an incubator maintained at 35° C. After 7, 14 and 28 days, the contents of the flask are passed through a 1 mm. screen to recover any undisintegrated material. The collected material is rinsed with tap water, removed from the screen and placed in a hot air (40° C.) to dry for at least 2 hours. The dried material is then weighed. The percent disintegration of the film sample in terms of percent weight loss is then determined based on the weight of the sample before and after immersion in the sludge. Final percent weight loss values are based on the average of three incubator runs, five samples per run (i.e., fifteen total film samples).

4. Resistance to Mold Based on Water Activity

The resistance to mold for the films of the present invention is based on visual signs of mold growth on the film during storage in an extreme hot/humid environment. Approximately 0.2 ml. of a medium containing mold spores ($1.0 \times 10^4$ cfu/ml) is dispensed directly onto the film. The film is then placed in a 26.7° C. environment having a relative humidity of 80% for 2 weeks. Film samples having no visible signs of mold growth after 2 weeks are considered to be resistant to mold growth.

5. Moisture Barrier Properties by Wet Through Test

The moisture barrier properties of the films of the present invention can be determined by a wet through test as follows: A catamenial pad using the film of the present invention as the backsheet is progressively loaded in 5 ml. increments at the 0, 5, 15 and 30 minutes points of the test until a maximum of 20 ml. of fluid is loaded on the pad. The pad is held under pressure during the test of 60 g. per cm$^2$). A test of duration of 50 min. is selected to allow sufficient time for slow migration of the test fluid through the film. The test fluid used is sheep's blood available from Cleveland Scientific. The passage of the test fluid through the backsheet of the pad is determined at the 5, 15, 30 and 50 min. points of test by measuring the amount of test fluid absorbed by cotton pads placed under the backsheet of the pad. The total amount of test fluid (in grams) measured at the 5, 15, 30 and 50 minutes points of the test represents the wet through of the pad.

EXAMPLES

Films according to the present invention can be prepared as follows:

Examples 1 to 6

Polymer blends of biodegradable Bionolle 3000, a polybutylene succinate adipate copolymer (Bionolle), with Polyox N-80, a water-soluble polyethylene oxide (PEO), are prepared in a twin screw extruder using the processing conditions shown in the following Table:

TABLE 1

| Processing Conditions | 25%/75% Blend of Bionolle/PEO | 85%/15% Blend of Bionolle/PEO |
| --- | --- | --- |
| Zone 1 | Off | Off |
| Zone 2 | 50° C. | 50° C. |
| Zone 3 | 101° C. | 74° C. |
| Zone 4 | 115° C. | 125° C. |
| Zone 5 | 135° C. | 129° C. |

TABLE 1-continued

| Processing Conditions | 25%/75% Blend of Bionolle/PEO | 85%/15% Blend of Bionolle/PEO |
| --- | --- | --- |
| Zone 6 | 109° C. | 109° C. |
| Die | 105° C. | 105° C. |
| Screw Speed | 150 rpm | 175 rpm |

Polymer blends of Eastar Biodegradable Copolyester 14776, a poly(tetramethylene) adipate-co-terephthalate copolyester (Eastar), with Polyox N-80, a water-soluble polyethylene oxide (PEO), are prepared in a twin screw extruder using the processing conditions shown in the following Table:

TABLE 2

| Processing Conditions | 70%/30% Blend of Eastar/PEO | 30%/70% Blend of Eastar/PEO | 10%/90% Blend of Eastar/PEO |
| --- | --- | --- | --- |
| Zone 1 | Off | Off | Off |
| Zone 2 | 50° C. | 75° C. | 50° C. |
| Zone 3 | 101° C. | 90° C. | 95° C. |
| Zone 4 | 104° C. | 98° C. | 107° C. |
| Zone 5 | 115° C. | 115° C. | 123° C. |
| Zone 6 | 96° C. | 93° C. | 101° C. |
| Die | 90° C. | 86° C. | 91° C. |
| Screw Speed | 175 mm | 150 rpm | 150 rpm |

Six films (Examples 1 to 6) are prepared with three layers (A, B and C) having the polymer compositions shown in the following Table:

TABLE 3

| Example | A Layer | B Layer | C Layer |
| --- | --- | --- | --- |
| 1 | 25%/75% Bionolle/PEO | 25%/75% Bionolle/PEO | 100% Bionolle |
| 2 | 60%/40% Bionolle/PEO* | 25%/75% Bionolle/PEO | 100% Bionolle |
| 3 | 60%/40% Eastar/PEO** | 30%/70% Eastar/PEO | 100% Eastar |
| 4 | 60%/40% Eastar/PEO** | 10%/90% Eastar/PEO | 70%/30% Eastar/PEO |
| 5 | 60%/40% Eastar/PEO** | 10%/90% Eastar/PEO | 100% Eastar |
| 6 | 30%/70% Eastar/PEO | 30%/70% Eastar/PEO | 100% Eastar |

*Homogeneous blend of appropriate amounts of 25%/75% and 85%/15% Bionolle/PEO blends
**Homogeneous blend of appropriate amounts of 70%/30% and 30%/70% Eastar/PEO blends Each of the films for Examples 1 to 6 are prepared in a David-Standard feed block extruder system having three extruders (A, B and C) for each of the respective layers, a Dow design feed block, a vertical die, a cast film chill roll and a winding system. The A and C extruders have a 1 inch orifice, while the B extruder has a 2 inch orifice. An air knife is use to help draw the resultant film onto the chill roll. (Talc is used as a processing aid in preparing the films of Examples 3 to 6.) The processing conditions shown in the following Table are used to prepare the respective films:

TABLE 4

| Example | Zone 1 (° F.) | Zone 2 (° F.) | Zone 3 (° F.) | Clamp (° F.) | Adapter (° F.) | Feed Block (° F.) | Die (° F.) | Speed (rpm) | Pressure (psi) |
|---|---|---|---|---|---|---|---|---|---|
| 1 | | | | | | | | | |
| A | 304 | 315 | 300 | — | 330 | | | 10.5 | 260 |
| B | 305 | 320 | 330 | 336 | 335 | 336 | 341 | 24.0 | 3320 |
| C | 310 | 315 | 330 | 335 | 335 | — | — | 5.3 | 1120 |
| 2 | | | | | | | | | |
| A | 304 | 315 | 330 | — | 330 | | | 1.7 | 540 |
| B | 305 | 320 | 330 | 336 | 335 | 336 | 341 | 24.1 | 3220 |
| C | 310 | 315 | 332 | 335 | 336 | | | 1.9 | 780 |
| 3 | | | | | | | | | |
| A | 298 | 305 | 320 | — | | | | 3.3 | 170 |
| B | 295 | 310 | 320 | 325 | 325 | 325 | 332 | 25.6 | 2210 |
| C | 295 | 308 | 316 | 325 | 326 | | | 7.7 | 370 |
| 4 | | | | | | | | | |
| A | 298 | 305 | 320 | — | 320 | | | 3.3 | 300 |
| B | 295 | 310 | 320 | 325 | 325 | 325 | 332 | 25.6 | 3040 |
| C | 295 | 300 | 316 | 325 | 326 | | | 7.6 | 490 |
| 5 | | | | | | | | | |
| A | 293 | 305 | 320 | — | 319 | | | 9.1 | 500 |
| B | 295 | 310 | 320 | 325 | 325 | 325 | 332 | 25.3 | 2340 |
| C | 300 | 305 | 310 | 325 | | | | 7.8 | 530 |
| 6 | | | | | | | | | |
| A | 295 | 305 | 320 | — | 320 | | | 10.6 | 600 |
| B | 295 | 310 | 320 | 325 | 325 | 325 | 332 | 24.1 | 2290 |
| C | 300 | 305 | 310 | 325 | 325 | | | 11.4 | 560 |

The properties of the films prepared for Examples 1 to 6 are shown in the following Table, along with the properties of films made with 100% Bionolle and 100% Eastar:

TABLE 5

| Example | Elongation CD (%) | Elongation MD (%) | Wet Through (grams) | Wt. Loss (%/7 days) | Mold Growth |
|---|---|---|---|---|---|
| 100% Bionolle | 710 | 610 | 0.12 | 0 | No |
| 100% Eastar | 580 | 690 | — | 0.8 | No |
| 1 | 480 | 390 | 0.11 | 62.6 | No |
| 2 | 60 | 450 | 0.21 | 65 | No |
| 3 | 300 | 690 | 0.14 | 53.6 | No |
| 4 | 240 | 640 | 0.28 | 77.3 | No |
| 5 | 110 | 320 | 0.27 | 75.9 | No |
| 6 | 310 | 730 | 0.27 | 62.1 | No |

Films prepared according to Examples 1 to 6 can be used as backsheets for disposable products such as absorbent interlabial pads or as apertured formed filmed for such products.

Examples 7 to 9

Polymer blends of Bionolle and Eastar, with Polyox N-80, are prepared in a twin screw extruder using the processing conditions shown in the following Table:

TABLE 6

| Processing Conditions | 25%/75% Blend of Bionolle/PEO | 40%/60% Blend of Bionolle/PEO | 25%/75% Blend of Eastar/PEO | 40%/60% Blend of Eastar/PEO |
|---|---|---|---|---|
| Zone 1 | 60° C. | 50° C. | 85° C. | 85° C. |
| Zone 2 | 105° C. | 105° C. | 100° C. | 100° C. |

TABLE 6-continued

| Processing Conditions | 25%/75% Blend of Bionolle/PEO | 40%/60% Blend of Bionolle/PEO | 25%/75% Blend of Eastar/PEO | 40%/60% Blend of Eastar/PEO |
|---|---|---|---|---|
| Zone 3 | 115° C. | 115° C. | 130° C. | 130° C. |
| Zone 4 | 160° C. | 172° C. | 180° C. | 188° C. |
| Zone 5 | 196° C. | 161° C. | 172° C. | 172° C. |
| Zone 6 | 125° C. | 133° C. | 143° C. | 148° C. |
| Die | 115° C. | 115° C. | 129° C. | 126° C. |
| Screw Speed | 150 rpm | 150 rpm | 150 rpm | 150 rpm |

Three films (Examples 7 to 9) are prepared with three layers (A, B and C) having the polymer compositions shown in the following Table:

TABLE 7

| Example | A Layer | B Layer | C Layer |
|---|---|---|---|
| 7 | 40%/60% Bionolle/PEO | 25%/75% Bionolle /PEO | 100% Bionolle |
| 8 | 40%/60% Eastar/PEO | 25%/75% Eastar/PEO | 100% Eastar |
| 9 | 40%/60% Eastar/PEO | 25%/75% Eastar/PEO | 100% Eastar |

Each of the films for Examples 7 to 9 are prepared in a David-Standard feed block extruder system having three extruders (A, B and C) for each of the respective layers, a Dow design feed block, a vertical die, a cast film chill roll and a winding system. The A and B extruders have a 1.5 inch orifice, while the C extruder has a 0.75 inch orifice. (Talc is used as a processing aid in preparing the films of Examples 8 to 9.) The processing conditions shown in the following Table are used to prepare the respective films:

TABLE 8

| Example | Zone 1 (° F.) | Zone 2 (° F.) | Zone 3 (° F.) | Clamp (° F.) | Adapter (° F.) | Feed Block (° F.) | Die (° F.) | Speed (rpm) | Pressure (psi) |
|---|---|---|---|---|---|---|---|---|---|
| 7 | | | | | | | | | |
| A | 310 | 335 | 350 | 350 | 350 | 350 | 350 | 2.1 | 1200 |
| B | 310 | 315 | 330 | 350 | 350 | — | — | 10.0 | 2100 |
| C | 335 | 345 | 357 | 380 | 380 | — | — | 18.0 | 1550 |
| 8 | | | | | | | | | |
| A | 310 | 335 | 350 | 35 | 350 | 350 | 350 | 2.1 | 900 |
| B | 310 | 315 | 330 | 350 | 350 | 336 | 341 | 10.0 | 1200 |
| C | 33 | 345 | 357 | 380 | 380 | | | 18.7 | 540 |
| 9 | | | | | | | | | |
| A | 310 | 335 | 350 | 350 | 350 | 350 | 350 | 2.1 | 900 |
| B | 310 | 315 | 330 | 350 | 350 | — | — | 10.0 | 1200 |
| C | 335 | 345 | 357 | 380 | 380 | — | — | 10.0 | 330 |

The percentage that the respective layers represent for the films prepared according Examples 7 to 9 are shown in the following Table, along with the properties of films made with 100% Bionolle and 100% Eastar:

TABLE 9

| Example | A Layer (%) | B Layer (%) | C Layer (%) |
|---|---|---|---|
| 7 | 15 | 70 | 15 |
| 8 | 20 | 60 | 20 |
| 9 | 20 | 70 | 10 |

Films prepared according to Examples 7 to 9 can be used as backsheets for disposable absorbent products such as absorbent interlabial pads or as apertured formed filmed topsheets for such products.

What is claimed is:

1. A film which is water-flushable and biodegradable, and which comprises:
   a. a first layer, which comprises:
      (1) from about 70 to 100% of a water-insoluble biodegradable thermoplastic polymer;
      (2) from about 20% to about 30% of a substantially water-soluble thermoplastic polymer; and
   b. a second layer adjacent the first layer, which comprises:
      (1) from about 60 to 100% of a substantially water-soluble thermoplastic polymer;
      (2) from 0 to about 40% of a water-insoluble biodegradable thermoplastic polymer;
   wherein the second layer is substantially thicker than the first layer;
   wherein the substantially water-soluble thermoplastic polymer is selected from the group consisting of hydroxypropyl cellulose, polyethylene oxide, polypropylene oxide, polyvinyl alcohol and copolymers, polyvinylpyrollidone, polyvinyl pyridine, gelatinized starch, interpenetrated networks of starch with ethylene/vinyl alcohol copolymers, nylon copolymers, polyethylene glycol, and mixtures thereof; and
   wherein the biodegradable polymer has a transition temperature ($T_g$) of about 20° C. or less and volume percent of crystallinity ($\Phi_C$) of from about 2 to about 65% and is selected from the group consisting of aliphatic polyalkylene succinate polymers, polyalkylene succinate adipate copolymers, aliphatic-aromatic copolyesters, polyesteramides and compatible mixtures thereof.

2. The film of claim 1 wherein the biodegradable polymer has a transition temperature ($T_g$) of about 0° C. or less and volume percent of crystallinity ($\Phi_C$) of from about 20 to about 40%.

3. The film of claim 1 wherein the water-soluble polymer is selected from the group consisting of polyethylene oxide and polyvinyl alcohol, and wherein the biodegradable polymer is selected from the group consisting of polybutylene succinate polymers and polybutylene succinate adipate polymers having weight-averaged molecular weights (Mw) of from about 40,000 to about 300,000, aliphatic-aromatic copolyesters comprising from 15 to 600 repeating units and selected from the group consisting of poly(tetramethylene succinate-co-terephthalate) copolyesters, poly(tetramethylene glutarate-co-terephthalate) copolyesters, poly(tetramethylene terephthalate-co-diglycolate) copolyesters, poly(tetramethylene glutarate-co-naphthalate) copolyesters and poly(tetramethylene) adipate-co-terephthalate copolyesters, and aliphatic polyesteramides prepared from combinations of adipic acid, butanediol or hexanediol and aminocaproic acid or ε-caprolactam having averaged molecular weights (Mw) of from about 50,000 to about 200,000.

4. The film of claim 1 which has a thickness of from about 0.5 to about 3 mil and wherein the second layer is at least 2 times as thick as each of the first and third layers.

5. The film of claim 4 wherein the first layer has a thickness of from about 0.1 to about 0.3 mil and wherein the second layer has a thickness of from about 0.6 to about 1.3 mil.

6. The film of claim 1 wherein the first layer comprises from about 5 to about 30% the thickness of the film; and wherein the second layer comprises from about 70 to about 95% of the thickness of the film and from about 70 to about 90% water-soluble polymer, and from about 10 to about 30% biodegradable polymer.

7. The film of claim 1 which has a percent elongation at break in either the machine direction (MD) or cross machine direction (CD) of at least 150%.

8. The film of claim 7 which has a percent elongation at break in either the machine direction (MD) or cross machine direction (CD) of at least 200%.

9. A disposable absorbent article comprising a topsheet, a backsheet made from the film of claim 1, and an absorbent core positioned between the topsheet and the backsheet such that the third layer of the film is adjacent the absorbent core.

10. A disposable absorbent pad insertable into the interlabial space of a female wearer, having a length, a width, a thickness, and a longitudinal centerline, the absorbent pad comprising:
   (a) a topsheet;
   (b) a backsheet made from the film of claim 1 and joined to the topsheet; and
   (c) an absorbent core positioned between the topsheet and the backsheet such that the third layer of the film is adjacent the absorbent core; wherein
      (1) the length of the absorbent pad is greater than about 60 mm and less than about 127 mm,
      (2) the width of the absorbent pad is between about 25 mm and about 40 mm,
      (3) the width and length of the absorbent pad each exceed the thickness of the absorbent pad,
      (4) the absorbent pad comprising an axis of preferred bending, such that when the absorbent pad is folded along the axis and inserted into the wearer's interlabial space the topsheet of the absorbent pad maintains contact with the walls of the wearer's labia.

11. The film of claim 1 which comprises at least a portion of an absorbent article, wherein the absorbent article is an incontinent brief, an incontinent pad, training pants, an diaper insert, a catamenial pad, a sanitary napkin, a pantiliner, a tampon applicator, a facial tissue, a paper towel, or a breast pads.

12. The film of claim 1 which comprises at least a portion of a flushable item, wherein the flushable item is a tampon applicator, a wrapper or a packaging for a disposable absorbent article.

13. The film of claim 1 wherein the substantially water soluble polymer is polyethylene oxide.

* * * * *

UNITED STATES PATENT AND TRADEMARK OFFICE
CERTIFICATE OF CORRECTION

PATENT NO. : 6,514,602 B1  
APPLICATION NO. : 09/520676  
DATED : February 4, 2003  
INVENTOR(S) : Zhao et al.

It is certified that error appears in the above-identified patent and that said Letters Patent is hereby corrected as shown below:

Column 3

Line 49, please delete "resent" and inser--present--.

Column 5

Line 55, please delete "hydroxhexanoate" and insert--hydroxyhexanoate--.

Column 14

Line 47, please delete "wearers" and insert--wearer's--.

Column 15

Line 52, please delete "20".

Column 20

Line 31, please delete "175 mm" and insert--175rpm--.

Column 21

Line 52, after "disposable", please insert--absorbent--.

Line 53, after "filmed", please insert--topsheets--.

Signed and Sealed this

First Day of August, 2006

JON W. DUDAS  
*Director of the United States Patent and Trademark Office*